US00PP13029P2

(12) United States Plant Patent
Whetman

(10) Patent No.: US PP13,029 P2
(45) Date of Patent: Oct. 1, 2002

(54) DIANTHUS PLANT NAMED 'SPANGLED STAR'

(76) Inventor: John Whetman, H. R. Whetman & Son, Houndspool, Ashcombe Road, Dawlish, Devon, EX7 0QP (GB)

( * ) Notice: Subject to any disclaimer, the term of this patent is extended or adjusted under 35 U.S.C. 154(b) by 0 days.

(21) Appl. No.: 09/637,104

(22) Filed: Aug. 10, 2000

(51) Int. Cl.[7] ..... A01H 5/00
(52) U.S. Cl. ..... Plt./272
(58) Field of Search ..... Plt./272, 263

(56) References Cited

U.S. PATENT DOCUMENTS

PP2,478 P * 2/1965 Mittleider ..... Plt./272

OTHER PUBLICATIONS

UOPV ROM GTITM Computer Database, GTI JOUVE Retrieval Software, 2001/02 citation for 'Spangled Star'.*

* cited by examiner

*Primary Examiner*—Bruce R. Campell
*Assistant Examiner*—Anne Marie Grünberg

(57) ABSTRACT

A new cultivar of Dianthus named 'Spangled Star' that is characterized in having fragrant, red flowers with two distinct pale pink blotches on each petal with a pale pink throat and margins. It has a profuse and extended flowering habit and a compact habit.

2 Drawing Sheets

BACKGROUND OF THE INVENTION

The present invention relates to a new and distinct cultivar of Alpine Dianthus and will be referred to hereafter as 'Spangled Star'. Alpine Dianthus are of hybrid origin and are hardy perennials grown for landscape use.

The new Dianthus resulted from a breeding program conducted by the inventor in Dawlish, Devon, England. The breeding project that resulted in the selection of 'Spangled Star', began in 1992 after growing and evaluating over 80 varieties of Dianthus. 'Spangled Star' was selected as a single plant amongst a unique group of Dianthus in the breeding program, "The Clock Series", so named for the unique color patterns of their flowers. 'Spangled Star' was selected as a single plant in 1994 by the inventor from seedlings that resulted from open crosses and back crosses made using an old variety, 'Queen of Henri' (unpatented), which is of hybrid origin.

'Spangled Star' was selected for its unique flower color combined with other desirable characteristics. The new variety of Dianthus is unique in having fragrant, red flowers with two distinct pale pink blotches on each petal with a pale pink throat and margins. It has a profuse flowering habit with 3–5 flowers per stem opening in succession. 'Spangled Star' can be further characterized by its compact habit; having freely branching upright shoots resulting in a neat mound of grey-green foliage. The new invention, 'Spangled Star', is unlike any other Dianthus known to the inventor. The closest comparison varieties are others that have arisen from the breeding program but have flowers with completely different color patterns. The antecedent variety, 'Queen of Henri' (unpatented), has a similar pattern to the flowers but the flower color is maroon as opposed to red, it is a taller plant, and has a shorter bloom period in comparision to 'Spangled Star'.

Asexual reproduction of the new cultivar was first accomplished by taking shoot cuttings in Dawlish, Devon, England in 1994 by the inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish this cultivar from other commercial varieties. 'Spangled Star' has not be tested under all possible conditions and phenotypic differences may be observed with variations in environmental, climatic, and cultural conditions:

1. The flowers of 'Spangled Star' are red with two pale pink blotches and a pale pink, serrated margin on each petal and a pale pink throat. The flowers have a clove fragrance.

2. 'Spangled Star' has a compact growth habit; it is freely branched and has a reduced height in comparision to the parent variety, 'Queen of Henri' (unpatented).

3. The foliage of 'Spangled Star' is grey-green and glaucous.

4. 'Spangled Star' has an extended bloom period in comparision to its parent and blooms in profusion in June and July with 3–5 flowers per stem opening in succession.

5. 'Spangled Star' is hardy at least to USDA Zone 5.

BRIEF DESCRIPTION OF THE DRAWING

The first drawing is of Dianthus 'Spangled Star' and shows the plant and flowering habit.

The second drawing shows a close-up of the flowers of 'Spangled Star'. All photographs were taken of plants grown in one-gallon containers under greenhouse conditions in Encinitas, Calif. The colors in these photographs are as accurate as possible by conventional photography.

BOTANICAL DESCRIPTION OF THE PLANT

The following is a detailed description of the new cultivar as grown in a one-gallon container under greenhouse conditions in Encinitas, Calif. The observed plant had been produced from shoot cuttings taken in the previous summer to the date of observation in May 2000. The plant had been overwintered at a night minimum temperature of 65 degrees Fahrenheit with day venting at 75 degrees Fahrenheit. The greenhouse was lightly shaded to an approximate light intensity of 5000 foot-candles. Day length was as naturally occurring in Southern California, approximately 13 hours during the month prior to flowering and observation. The color determination is in accordance with The R.H.S. Colour Chart of The Royal Horticultual Society, London, England, except where general color terms of ordinary dictionary significance are used.

Botanical classification: Dianthus 'Spangled Star' is a cultivar of Alpine Dianthus and is of hybrid origin.

Commercial classification: Hardy Perennial and is suitable as a container plant.

Parentage: Unnamed parents from a population derived from open crossing and back crossing of unnamed cultivars also including the antecedent variety Dianthus 'Queen of Henri'.

Plant description:

*Blooming habit and period.*—Blooms from June–July in profusion with 3–5 flowers per stem opening in succession on stems 17–22 cm in height.

*Lastingness of the blooms.*—Individual blooms last from 7 days at a temperature of 70° F. to 10 days at a temperature of 50° F.

*Plant habit.*—Compact, mound form, clump-forming.

*Height and spread.*—17–22 cm in height and spread.

*Hardiness.*—Zone 5 (possibly 4).

*Type.*—Evergreen perennial herb.

*Root system.*—Fibrous.

*Propagation.*—Shoot cuttings.

*Culture.*—Garden: Sunny location in well-drained but moist, moderately fertile soils, with a PH of 6.4–6.8. Grower: Well aerated growing media, good ventilation, and low humidity.

*Diseases and pests.*—All stock has been virus indexed stock. Susceptible to Carnation Ring Spot, Carnation Rust if foliage is kept wet and *Alternaria dianthi* if grown under high humidity. Not resistant to commonly occurring diseases of Dianthus.

Stems:

*Shape.*—Round.

*Size.*—1.5–3.0 mm in diameter, 3 mm at nodes.

*Surface.*—Glaucous.

*Color.*—137A

*Branching.*—Numerous basal breaks.

*Internode length.*—Congested, 0.5–1.0 cm.

*Peduncles.*—12–14 cm in length, 1.5–2.0 mm in width, 137A in color, strong but pendulous habit.

*Pedicels.*—3–5/peduncle, 1.5–2.5 cm., 1.0 mm, 137A in color.

Leaves:

*Shape.*—Linear.

*Division.*—Simple.

*Apex.*—Acute.

*Base.*—Decurrent.

*Venation.*—Not prominent.

*Margins.*—Entire.

*Arrangement.*—Opposite.

*Surface.*—Glaucous (upper and lower surface).

*Size.*—5–8 cm in length, 2–3.5 mm in width.

*Color.*—Upper and lower surface; young leaves 137C, mature leaves 189A.

*Fragrance.*—None.

Flowers:

*Type.*—Salviform, 3–5/peduncle, symmetrical, determinate.

*Size.*—3.6–4.0 cm in diameter, 2.5–3.0 cm in height (including calyx).

*Fragance.*—Clove scented.

*Petals.*—5, apopetalous, wedge-shaped, slightly overlapping to separate.

*Margins.*—Serrated, 1-2-3 mm wide.

*Size.*—1.9–2.1 cm in length, 1.4 cm (at base) to 1.6 cm in width, throat 4–5 mm cm in length, blotches (2/petal) are 2.5 mm in width and 4–6 mm in length.

*Color* (*upper surface*).—Petal base 73A, blotches, throat and margins 65D to white.

*Color* (*lower surface*).—51D except that underside of blotches throat and margins is 67D.

*Calyx.*—1 calyx with 5 synsepalous, persistent, notched lobes 0.4 mm deep and 0.3 mm wide, lustrous surface, size; 2.0–2.5 cm in length, 0.4–0.6 cm in width, color; 137D, Epicalyx present 4–5 mm in height.

*Reproductive organs.*—Stamens; 10, 2 whorls, stamens of outer whorl are shorter, apostemonous, distinct, develop after pistil developement (self incompatible), exserted, many are aborted.

*Pistil.*—1, 2 stigmas, style color white, protruding 1.0–1.2 cm above petals, ovary is superior.

*Seed production.*—The seed capsule is cylindrical with a point which opens on maturity to become a circular hole for seed dispersion. The capsule is approximately 6 mm long and 3 mm wide. It is pale green initially becoming brown on maturity. The seed number varies from 1–15 and the seed is 1.5 mm in diameter, wrinkled and black. The seed is usually fertile.

I claim:

1. A new and distinct cultivar of Dianthus plant named 'Spangled Star' as described and illustrated.

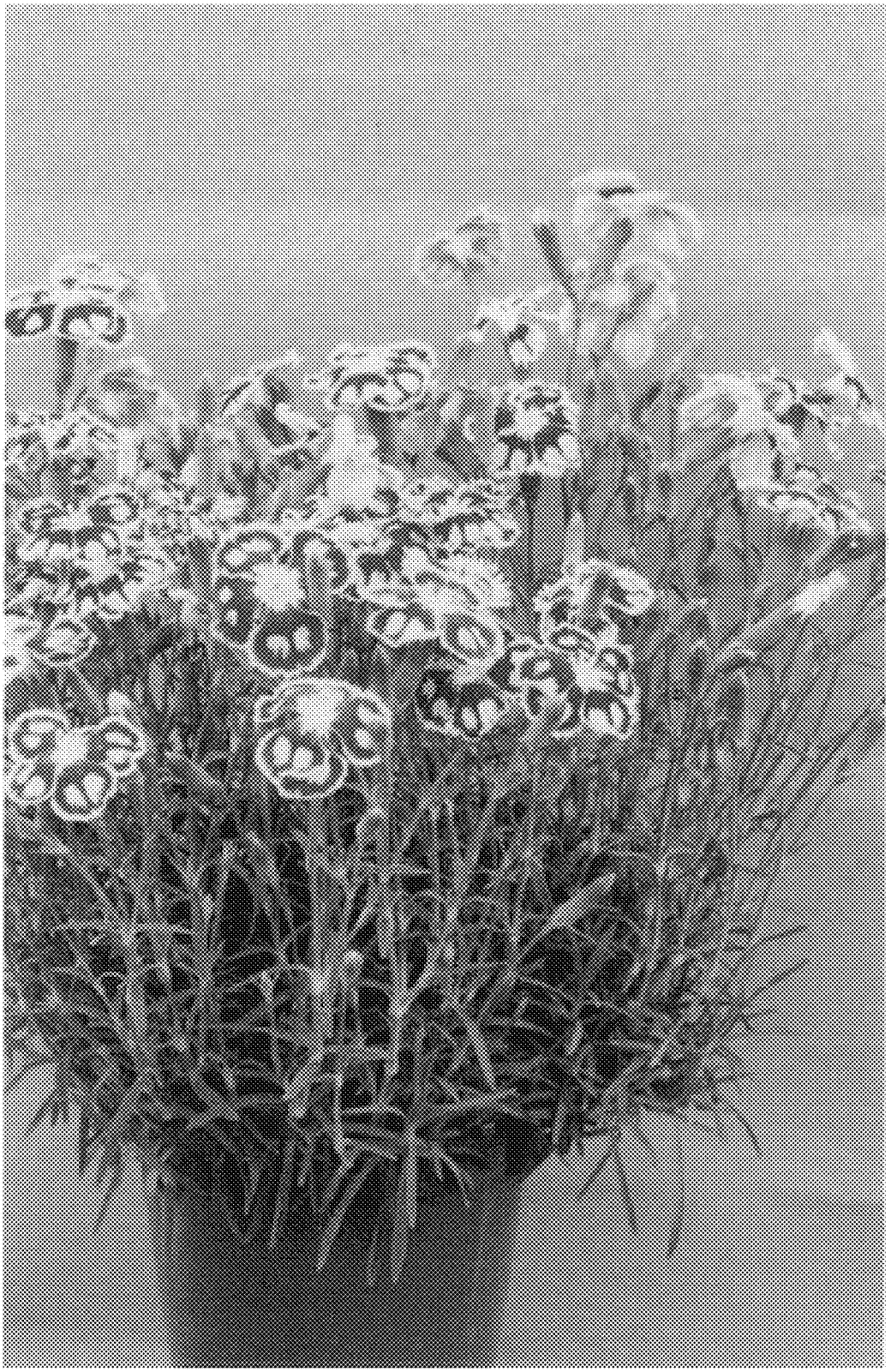

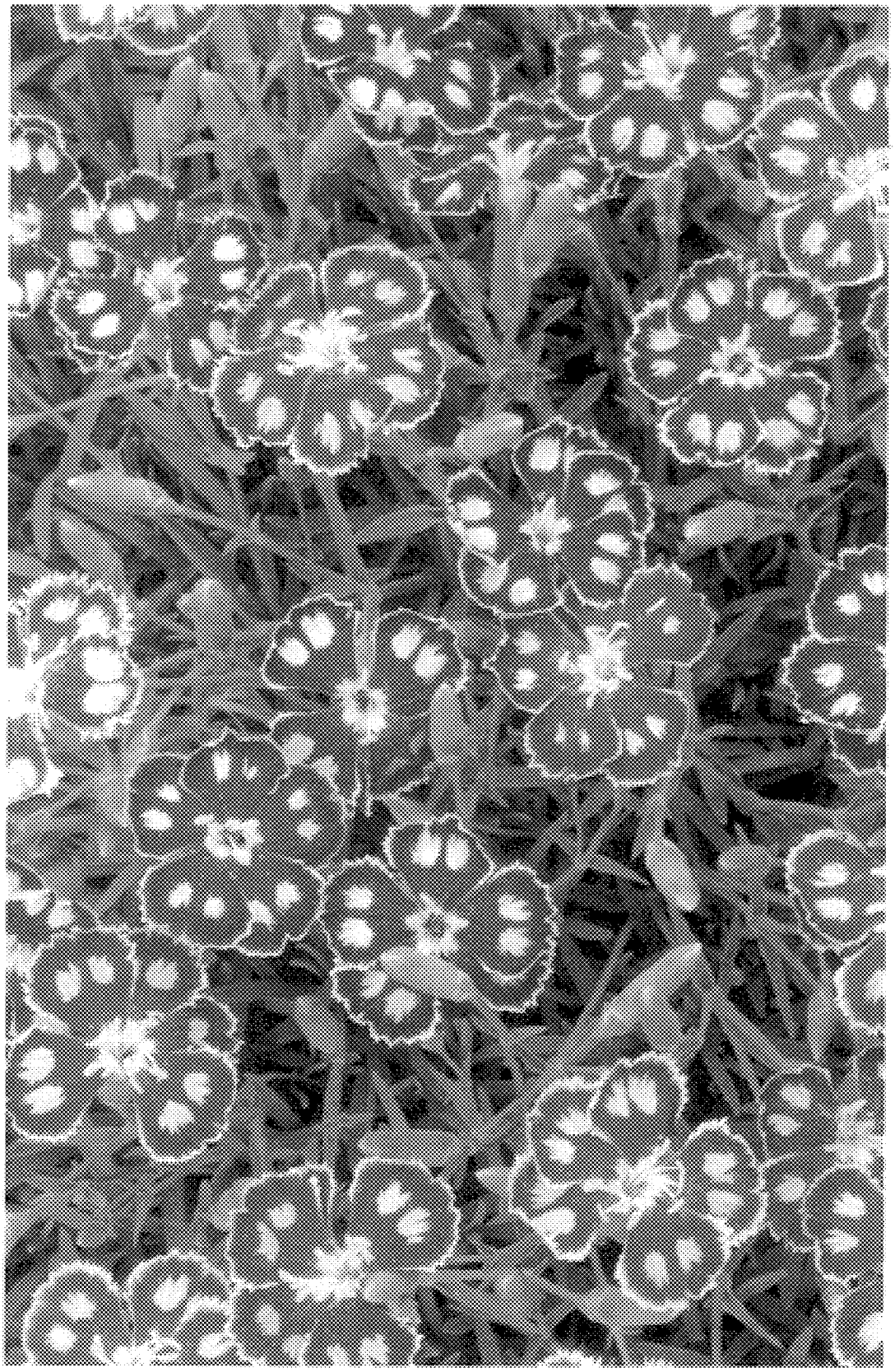

* * * * *